United States Patent [19]
Abell et al.

[11] Patent Number: 5,206,135
[45] Date of Patent: Apr. 27, 1993

[54] USE OF THE OXYGENASE ACTIVITY OF ACETOLACTATE SYNTHASE FOR HERBICIDE DETECTION

[75] Inventors: Lynn M. Abell, New Castle; John V. Schloss, Wilmington, both of Del.

[73] Assignee: E. I. du Pont de Nemours and Company, Wilmington, Del.

[21] Appl. No.: 635,013

[22] Filed: Dec. 28, 1990

[51] Int. Cl.$^5$ .......................... C12Q 1/00; C12Q 1/26
[52] U.S. Cl. .......................................... 435/4; 435/25; 435/189; 435/190; 435/817
[58] Field of Search .................. 435/4, 25, 189, 190, 435/817

[56] References Cited

PUBLICATIONS

Schloss et al, *Biochemistry*, vol. 24, pp. 4952–4959, 1985.
Schloss et al, *Nature*, vol. 331, pp. 360–362, 1988.
Kobos et al, *Trends in Biotechnology*, vol. 7, pp. 101–105, 1989.
Sweet et al, *Analytical Biochemistry*, vol. 107, pp. 337–340, 1980.
Pelczar & Reid, Microbiology (McGraw-Hill, New York, 1972, pp. 159–162).
Enzyme Nomenclature 1978, Recommendations of the Nomenclature Committee of the International Union of Biochemistry on the Nomenclature and Classification of Enzymes, Academic Press.

*Primary Examiner*—Michael G. Witshyn
*Assistant Examiner*—Abdel A. Mohamed

[57] ABSTRACT

A process for the detection of herbicides that inhibit acetolactate synthase (EC 4.1.3.18) by use of the enzyme, a suitable substrate (pyruvate, α-aceto-lactate, α-ketobutyrate, or α-aceto-α-hydroxybutyrate), and an oxygen-sensitive electrode is disclosed.

7 Claims, No Drawings

USE OF THE OXYGENASE ACTIVITY OF ACETOLACTATE SYNTHASE FOR HERBICIDE DETECTION

BACKGROUND OF THE INVENTION

1. Field of the Invention

This invention relates to the process of detecting herbicides that inhibit acetolactate synthase (EC 4.1.3.18) by use of acetolactate synthase and an oxygen-sensitive electrode.

2. Summary of the Background

The herbicidal activity of a number of commercial herbicides is known to be due to their inhibition of the enzyme acetolactate synthase (Schloss, et al., Nature 331:360 (1988)). There is a need by the companies that sell these herbicides and the people that use them to be able to detect the presence of residual herbicides in areas of their usage. The present invention discloses a process for detecting these herbicides by their ability to inhibit the consumption of oxygen by pyruvate, α-acetolactate, α-ketobutyrate, or α-aceto-α-hydroxybutyrate in the presence of acetolactate synthase (Schloss et al., Biochemistry 24:4952 (1985).

SUMMARY OF THE INVENTION

The present invention provides a process for the detection of herbicides that inhibit acetolactate synthase by the ability of these substances to reduce the rate of oxygen consumption by pyruvate, α-acetolactate, α-ketobutyrate, or α-aceto-α-hydroxybutyrate supported by acetolactate synthase. When solutions containing pyruvate, α-acetolactate, αketobutyrate, or α-aceto-α-hydroxybutyrate are brought in contact with an oxygen-sensitive electrode, any oxygen present in these solutions will be consumed upon the addition of acetolactate synthase and the required cofactors for this enzyme (flavin adenine dinucleotide, thiamine pyrophosphate, and a divalent metal, such as $Mg^{2+}$). Herbicides that inhibit the normal function of this enzyme will prevent or retard the consumption of oxygen if present in these solutions.

DETAILED DESCRIPTION OF THE INVENTION

The present invention provides processes for the detection of those herbicides that inhibit acetolactate synthase. It comprises mixing a solution to be tested for the presence of herbicides with an aqueous solution of pyruvate, α-acetolactate, α-ketobutyrate, or α-aceto-α-hydroxybutyrate. This mixture is then brought in contact with acetolactate synthase (Schloss et al., Biochemistry 24:4952 (1985)) and an oxygen-sensitive electrode. Acetolactate synthase can be added to the final detection solution as an aliquot of an aqueous solution, or immobilized to a inert support by standard procedures (Kobos et al. Trends Biotechnol. 7:101 (1989)) and placed in close proximity to the oxygen-sensitive electrode. Also added to the final detection solution are the required components of the acetolactate synthase reaction, flavin adenine dinucleotide, thiamine pyrophosphate, $Mg^{2+}$ or other suitable metal (Schloss et al., Biochemistry 24:4952 (1985)), and a buffer to control the pH of the detection solution (optimally, but not restricted to, pH 8). A slower rate of oxygen consumption, in the presence of solutions being tested, indicates the presence of inhibitors of acetolactate synthase. Inhibition of the oxygenase activity can be used to quantitate the level of contamination, if the identity of the herbicide is known by comparison with standard solutions.

The reactions carried out by acetolactate synthase (Schloss et al., Biochemistry 24:4952 (1985)) involving pyruvate, α-acetolactate, $CO_2$, and $O_2$ are illustrated below. By isotopic labelling studies with $H_2^{18}O$ and $^{18}O_2$, the identity of the common product of the oxygen consuming reactions has been established as peracetate. The oxygen consuming reaction of acetolactate synthase, and its potential application in an electrode-based assay for herbicides, has not been previously recognized.

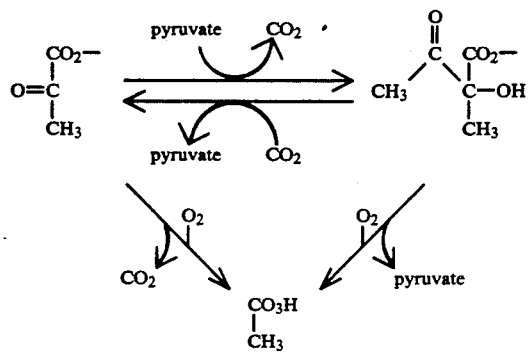

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Examples 1-3 demonstrate the level of oxygenase activity obtained with pyruvate, α-ketobutyrate, or α-acetolactate. Examples 4-5 demonstrate that the oxygenase activity, like the known synthetic reactions of the enzyme, is sensitive to inhibition by herbicides.

EXAMPLES 1-3

The Oxygenase Activity of Acetolactate Synthase

To a 1 ml solution containing 0.1 M tricine-NaOH, pH 8, 10 mM $MgCl_2$, 0.1 mM thiamine pyrophosphate, and 0.1 mM flavin adenine dinucleotide were added various concentrations of pyruvate (10 μM to 10 mM), α-keto-butyrate (10 μM to 80 mM), or acetolactate (0.15 to 5.5 mM). After allowing the solution to equilibrate with air (21 % $O_2$), the level of dissolved oxygen was monitored by use of a commercially available oxygen-sensitive electrode (Hansatech) and polarographic electronics as described by Sweet et al. (Analytical Biochemistry 107:337 (1980)). In the absence of further additions, negligible oxygen was consumed over a 30 minute period. To initiate the consumption of oxygen, 20 μl of a 2 mg/ml stock solution of acetolactate synthase was added if pyruvate or α-acetolactate were used as substrate, or 5 μl of a 49 mg/ml stock solution of acetolactate synthase was added if α-ketobutyrate was used as substrate. The limiting rate of oxygen consumption at saturating concentrations of pyruvate, α-ketobutyrate, or α-acetolactate are illustrated in Table 1. The concentrations of α-acetolactate or α-ketobutyrate that gave half of the maximum rate (the Michaelis constant) were 1.4 mM and 32 µM, respectively. The rate of oxygen consumption was constant over the range of concentrations of pyruvate examined, indicating that the Michaelis constant for this substrate was substantially lower than 10 µM.

TABLE 1

The Oxygenase activity of Acetolactate Synthase with Different Substrates

| Example | Substrate | Maximum rate (µmoles of oxygen consumed/ mg enzyme/min) |
|---|---|---|
| 1 | Pyruvate | 0.14 |
| 2 | α-Ketobutyrate | 0.022 |
| 3 | α-Acetolactate | 0.20 |

EXAMPLES 4–5

Sensitivity of the Oxygenase Activity to Herbicides

Assays were conducted as described under Examples 1–3, except that 100 µM pyruvate was used as substrate. Rates of oxygen consumption obtained in the absence of added herbicide were compared to the rates obtained in the presence of sulfometuron methyl (0.25 to 5 µM) or chlorsulfuron (0.25 to 1 µM), two of the commercial sulfonylurea herbicides that inhibit this enzyme. The concentration of herbicide that gave 50 % inhibition is shown in Table 2. These values are similar to previously reported values (Schloss et al. Nature 331:360 (1988)) for inhibition of the enzyme monitored by use of the known acetolactate-forming reaction.

TABLE 2

Sensitivity of the Oxygenase Activity of Acetolactate Synthase to Herbicides

| Example | Compound | Concentration that Gives 50% Inhibition (µM) |
|---|---|---|
| 4 | chlorsulfuron | 0.5 |
| 5 | sulfometuron methyl | 1.0 |

What is claimed is:

1. A process for detecting acetolactate synthase-inhibiting herbicides by the use of acetolactate synthase and an oxygen-sensitive electrode, which comprises mixing a solution to be tested with a substrate selected from the group consisting of pyruvate, α-ketobutyrate, α-acetolactate, and α-aceto-α-hydroxybutyrate;

placing the mixture in contact with an oxygen-sensitive electrode;

adding to the mixture an acetolactate synthase, in soluble form or immobilized to an inert support;

adding to the mixture flavin adenine dinucleotide, thiamine pyrophosphate, a divalent metal, and a buffer to control the pH of the solution to the physiologic range of 6 to 10 pH; and monitoring the consumption of oxygen by the ensuing reaction by use of the oxygen-sensitive electrode.

2. A process according to claim 1 wherein the substrate is pyruvate.

3. A process according to claim 1 wherein the substrate is α-ketobutyrate.

4. A process according to claim 1 wherein the substrate is α-acetolactate.

5. A process according to claim 1 wherein the substrate is α-aceto-α-hydroxybutyrate.

6. The process according to claim 1 wherein the optimal pH of the solution is controlled to about 8.0.

7. The process according to claim 1 wherein the divalent metal is $Mg^{2+}$.

* * * * *